United States Patent [19]

Blackburn et al.

[11] 4,270,564

[45] Jun. 2, 1981

[54] PURGING SYSTEM

[75] Inventors: Wayne E. Blackburn; Max D. Liston, both of Irvine; William A. Stark, Costa Mesa, all of Calif.

[73] Assignee: Liston Scientific Corp., Newport Beach, Calif.

[21] Appl. No.: 927,372

[22] Filed: Jul. 24, 1978

[51] Int. Cl.³ .............................................. A61B 5/08
[52] U.S. Cl. ................................. 137/240; 134/57 R; 134/166 C; 137/624.11
[58] Field of Search .................... 134/57 R, 166 C; 128/716; 200/61.04, 61.05, DIG. 40; 137/237–241

[56] References Cited

U.S. PATENT DOCUMENTS

| 3,259,891 | 7/1966 | Coulter et al. | 137/240 X |
| 3,802,417 | 4/1974 | Lang | 128/716 |

Primary Examiner—Gerald A. Michalsky
Assistant Examiner—Richard Gerard
Attorney, Agent, or Firm—Raymond L. Madsen

[57] ABSTRACT

There is disclosed a purging system for removing foreign matter from a fluid conducting conduit in which a sensor detects the presence of the foreign matter and produces an electrical signal which activates a timer which, in turn, connects a pump to the conduit for a given time duration to purge the conduit of the foreign matter. A counter also maybe connected to periodically activate the timer and purge the conduit, whether or not the sensor has detected foreign matter.

11 Claims, 9 Drawing Figures

PURGING SYSTEM

The present invention relates to purging systems for fluid conducting conduits and more particularly to purging apparatus for removing moisture from gas lines in respiratory monitoring systems.

In the field of respiration monitoring, it has been the general practice to employ pump and vacuum equipment to remove mucous and moisture from the respiratory gas lines of the system introduced by coughing spasms and edema of the patient so that the respiratory gasses may flow freely through the lines. Although such equipment has served the purpose, it has not proved entirely satisfactory under all conditions of service for the reasons that considerable difficulty has been experienced in sensing or detecting the presence of moisture and mucous in the lines and difficulties encountered in minimizing the number of components and cost of a purging system.

Those concerned with the development of purging systems for respiratory monitoring apparatus have long recognized the need for a simple and reliable moisture sensor or detector coupled with a system of electrical and mechanical components which efficiently and economically purge the respiratory gas lines and remove drops of moisture and mucous. The present invention fulfills this need.

One of the most critical problems confronting designers of respiratory monitoring purging systems has been the design of a reliable and low cost moisture sensor or detector. This problem is overcome by the present invention.

The general purpose of this invention is to provide a purging or moisture removal system which embraces all the advantages of similarly employed purging apparatus and equipment and possesses none of the aforedescribed disadvantages. To attain this, the present invention contemplates a simple low cost and reliable moisture sensor in combination with an electrical counter and timer circuit whereby unreliable detection of moisture and the undetected clogging of respiratory monitoring gas lines are avoided.

An object of the present invention is the provision of a gas conduit purging system which is activated by a simple and reliable conductivity moisture sensor.

Another object is to provide a purging system for gas lines in a respiratory monitoring system which is activated periodically to remove moisture and mucous.

A further object of the invention is the provision of a purging system which is activated by the presence of moisture to purge respiratory monitoring system gas lines of moisture and mucous over an adjustable duration of time.

Still another object is to provide a respiratory gas line purging system which is periodically activated to remove moisture and mucous in addition to being activated upon the detected presence of moisture and mucous.

Other objects and many of the attendant advantages of this invention will be readily appreciated as the same becomes better understood by reference to the following detailed description when considered in connection with the accompanying drawings in which like reference numerals designate like parts throughout the figures thereof and wherein;

Figure 1:
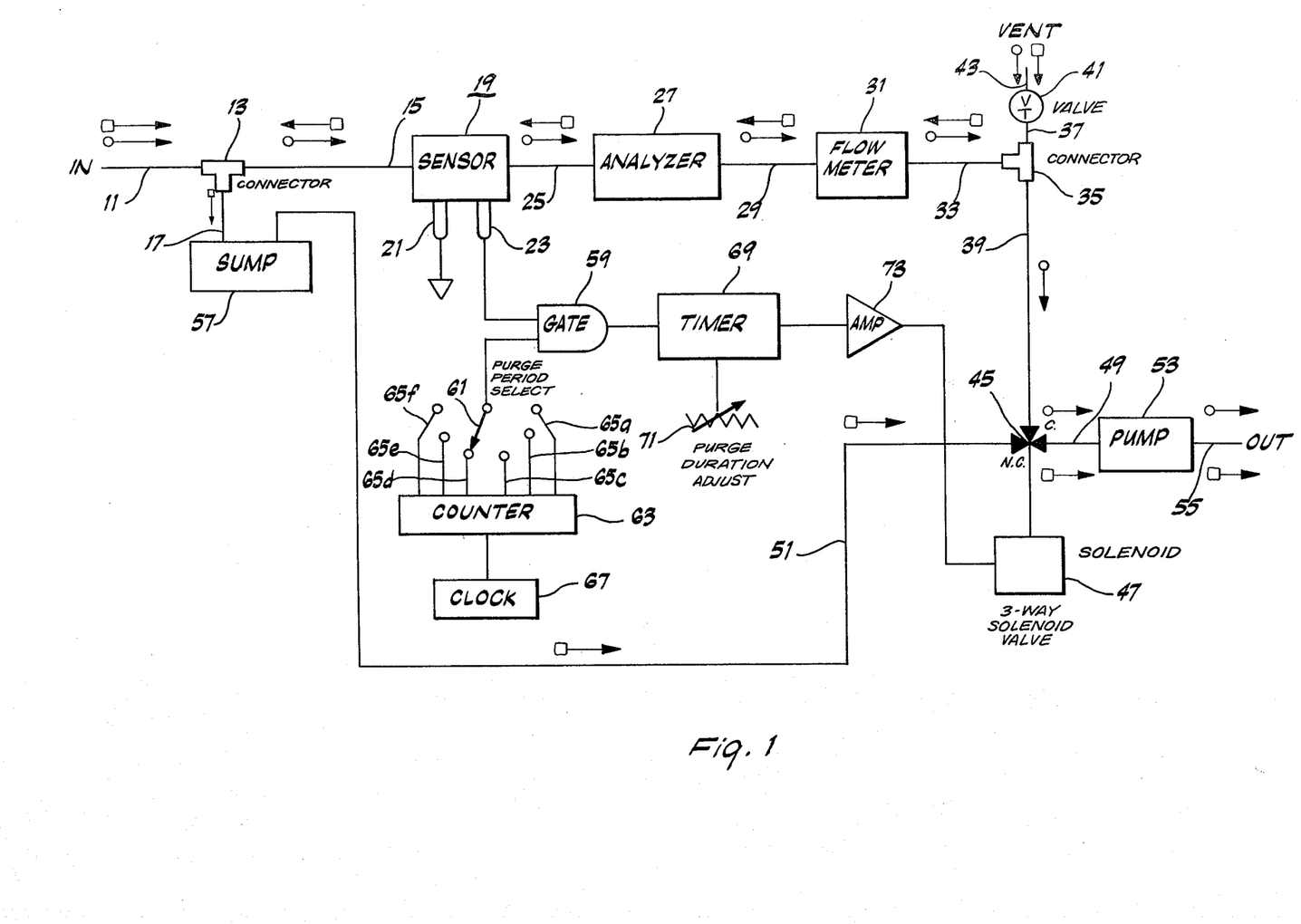
FIG. 1 shows a block diagram of the elements comprising a preferred embodiment of the invention.

Referring now to the drawings wherein like reference characters designate like or corresponding parts throughout the several views, there is shown in FIG. 1 (which illustrates a preferred embodiment) a fluid conduit or input gas line 11 which is adapted to be connected to a source of gas or fluid such as a respiratory system for analysis of respiratory gasses. Conduit 11 in turn is connected to a fluid or gas line connector 13 which connects conduit 11 to fluid or gas line conduits 15 and 17. Conduit 15 is connected to a moisture or foreign material sensor 19 having a pair of electrodes 21 and 23 extending therefrom and which is further connected by a conduit 25 to a gas or fluid analyzer 27. Analyzer 27 is further connected by a conduit 29 to a flow meter 31 which, in turn, is connected by a conduit 33 to a connector 35. Connector 35 connects conduit 33 to a conduit 37 and a conduit 39, conduit 37 being in turn connected to an adjustable or throttle valve 41, which is connected to a vent conduit 43. Conduit 39 is connected to a 3-way solenoid valve 45 which is activated by a solenoid 47. 3-way solenoid valve 45 normally connects conduit 39 with a conduit 49 and upon operation of solenoid 47, connects conduit 49 with a conduit 51. Conduit 49 is further connected to a pump 53 which in turn is connected to a conduit 55. Conduit 51 is further connected to the output conduit or tube of a sump container 57 which in turn has an input tube connected to conduit 17.

Electrode 21 of sensor 19 is connected to a common ground and electrode 23 of sensor 19 is connected to one of two inputs to an electrical gate 59. The other input of gate 59 is connected to a purge period select switch 61 which in turn is connected to an electrical counter 63 through any one of a plurality of counter output terminals 65a through 65f. Conduit 63 is further connected to a clock 67 which provides a source of electrical pulses to be counted by counter 63.

The output of gate 59 is further connected to an electrical timer 69 having a variable resistance 71 for adjusting purge duration. Timer 69 is further connected to an amplifier or driver 73 which in turn is connected to solenoid 47 to actuate solenoid 47.

It should be noted that analyzer 27 may be any one of a well known variety of gas analyzers utilized for the analysis of respiratory gasses, and that flow meter 31 may be one of the well known flow meter varieties used to monitor the flow of respiratory gasses. Pump 53 may be of the well known rotating vane or blade type as well as a reciprocating piston type pump or one of the other types of well known vacuum pumps utilized to move gaseous components through a system of conduits and gas devices. Pump 53 may also be the vacuum system of a hospital instead of a specific pump device. Sump 57 may be a container of the type well known in the gas analysis field for the trapping and collecting of moisture and foreign matter. Clock 67 may be any stable source of alternating voltage or current well known in the field of electronics and counter 63 may be a conventional electronic counter circuit which produces periodic signals of different frequency at each of its plurality of output terminals such as RCA CD-4020. Gate 59 may be a conventional semi-conductor "AND" gate such as National Semiconductor 74 CO8 and timer 69 may be a well known electronic timing circuit such as a monostable flip-flop with adjustable duration or a Signetics 555. Amplifier 73 can be a conventional semi-conductor amplifier such as a transistor for driving the coil of solenoid 47.

Figures 2, 3, 4:
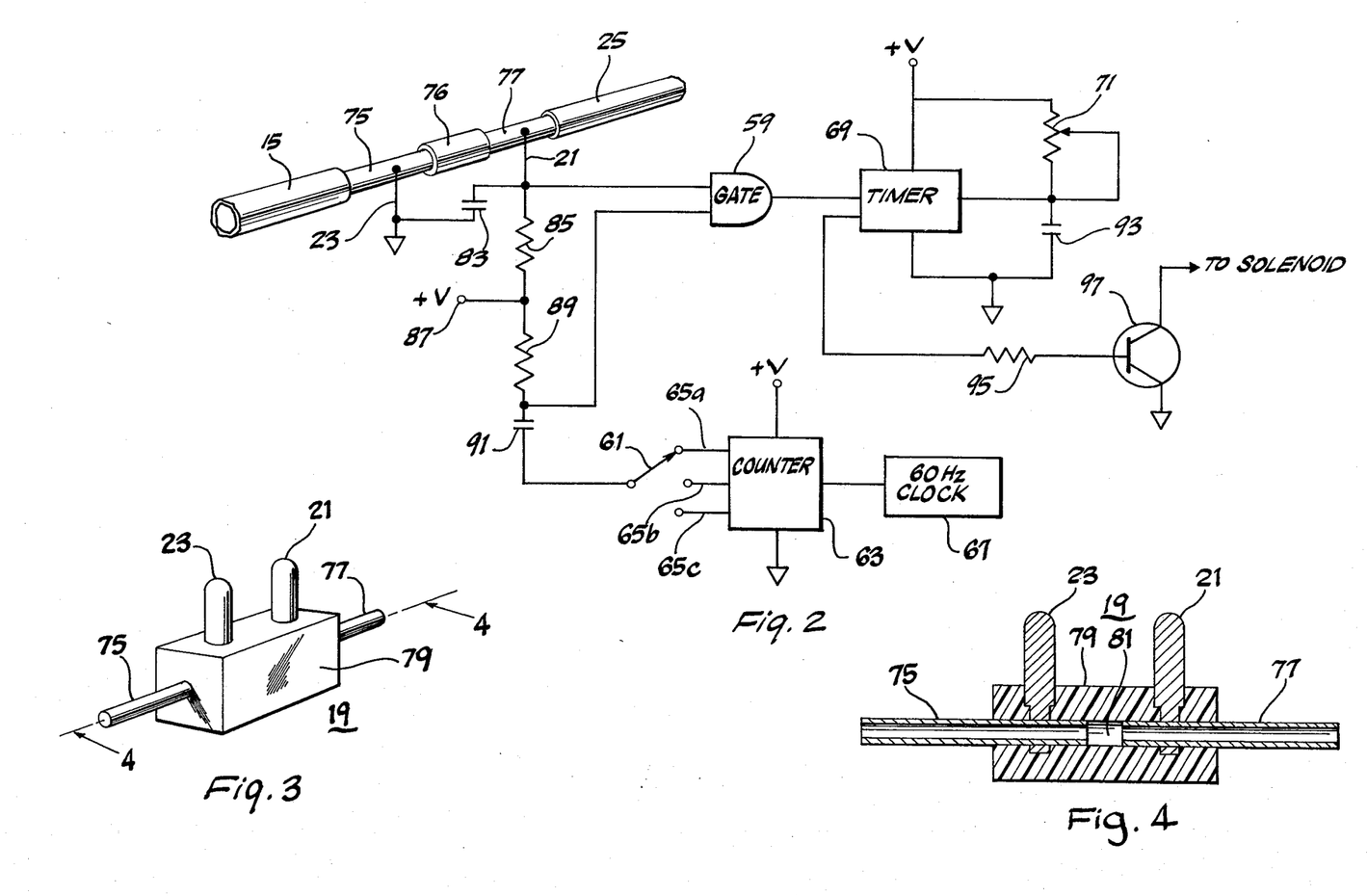
FIG. 2 illustrates a partial diagrammatic, circuit and block diagram of some of the elements of FIG. 1.
FIG. 3 illustrates a diagrammatic view of the moisture sensor of FIG. 1.
FIG. 4 illustrates a cross-section of the sensor of FIG. 3 taken along line 4—4 of FIG. 3 in the direction of the arrows.

Turning now to FIG. 2 there is illustrated diagrammatically a sensor having a pair of fluid or gas conduits 75 and 77 which are electrically conductive and which are separated by an insulating conduit 76. Electrically conductive conduit 75 in turn is connected to conduit 15, and electrically conductive conduit 77 in turn is connected to conduit 25. Electrode 23 which is connected to conduit 75 is further connected to a common ground and electrode 21 which is connected to conduit 77 is connected to a capacitor 83 which in turn is connected to electrode 23. Electrode 21 is further connected through a resistor 85 to a source of positive voltage +V through a terminal 87. Terminal 87 is further connected through a resistor 89 to one side of a capacitor 91 which in turn is connected to switch 61 which in turn selects any one of the various outputs 65a-65c from counter 63 which in turn is activated by 60 Hz clock 67.

One input to gate 59 is connected to the junction of capacitor 83 and resistor 85 and the other input to gate 59 is connected to the junction of capacitor 91 and resistor 89. Timer 69 is connected to the output of gate 59 and also is further connected to a source of voltage +V and further is connected to a variable resistor 71 and a capacitor 93 which capacitor also is connected to common ground along with one terminal of timer 69. The output of timer 69 is further connected through a resistor 95 to the base of a transistor 97 having the emitter thereof connected to the common ground and the collector thereof is connected to solenoid 47 of the 3-way solenoid valve.

FIG. 3 shows a diagrammatic view of sensor 19 illustrating an insulating body 79 housing and insulatively supporting in series and spacing apart electrically conductive gas conduits 75 and 77 which are respectively connected (not visible) to electrodes 23 and 21 extending at right angles therefrom and protruding from body 79. Sensor 19 is made from low cost materials and by economical fabrication methods so as to be disposable for reasons hereinafter stated.

A more detailed cross section view of sensor 19 is illustrated in FIG. 4. Insulating body 79 holds electrically conductive conduits 75 and 77 separated by a hollow gap 81. Electrode 23 is imbedded in insulating body 79 and has a hole therethrough through which electrically conductive conduit 75 passes and which is electrically connected thereto. Similarly, electrode 21 is imbedded in insulating body 79 and has a hole therethrough through which electrically conductive conduit 77 and is electrically attached thereto.

Figure 5:
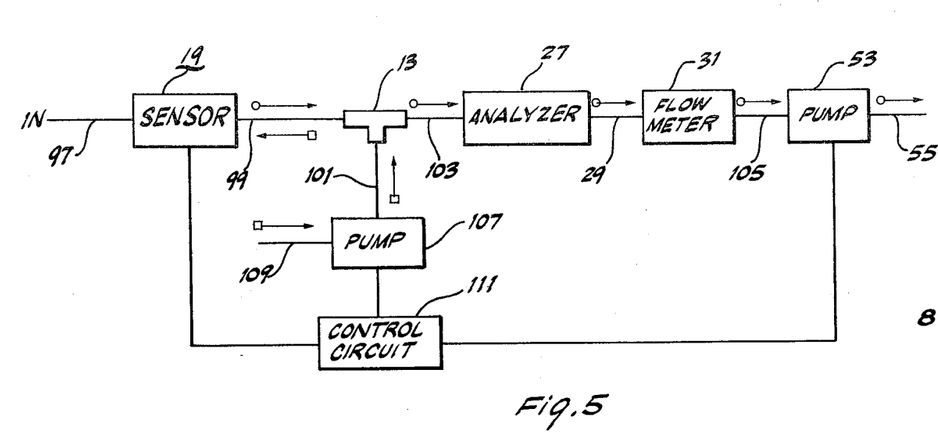
FIG. 5 shows a block diagram of the components comprising an alternate embodiment of the invention with the sensor at the input to the system and with two pumps.

In FIG. 5, sensor 19 is connected to an input conduit 97, which may be a catheter connected to a patient. A conduit 99 connects sensor 19 to connector 13 which in turn connects conduit 99 to conduits 101 and 103. Conduit 103 is connected to analyzer 27 which in turn is connected by conduit 29 through flowmeter 31 to a conduit 105. Conduit 105 is connected to vacuum pump 53. Conduit 86 is connected to a pressure pump 107 which which in turn has an inlet conduit 109. Sensor 19 is electrically connected to a control circuit 111 which in turn activates pump 107 when moisture is present in sensor 19 and activates pump 53 when no moisture is present.

Figure 6:
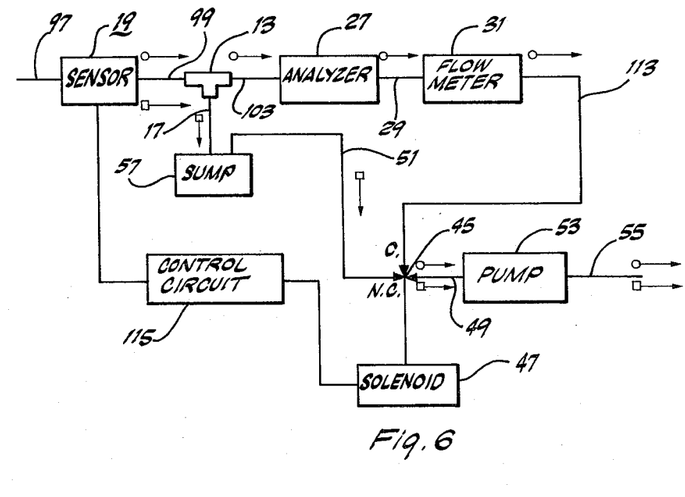
FIG. 6 illustrates a block diagram of the components of another embodiment of the invention with the sensor at the input to the system and a single pump.

FIG. 6 illustrates substantially the same arrangement of components shown in FIG. 1 with adjustable valve 41 being removed and Sensor 19 being relocated in the input line. Conduit 97 is connected through Sensor 19 to Conduit 99 which in turn is connected through connector 13 to a conduit 103 and conduit 17. Conduit 103 is connected through analyzer 27, conduit 29 and flowmeter 31 to a conduit 113. Conduit 113 in turn is connected to three-way solenoid valve 45 which normally connects conduit 113 to pump 53. Sensor 19 is electrically connected to a control circuit 115, which includes the electrical circuitry of FIG. 1. Control Circuit 115 is further connected to solenoid 47 of three-way solenoid valve 45.

It should be noted that in both FIGS. 5 and 6 Sensor 19 is required to be disposable since moisture accumulated therein is pumped during purge in the reverse direction through the patient's catheter tube or conduit. Therefore, Sensor 19 can only be used for one patient for this reason.

Figure 7:
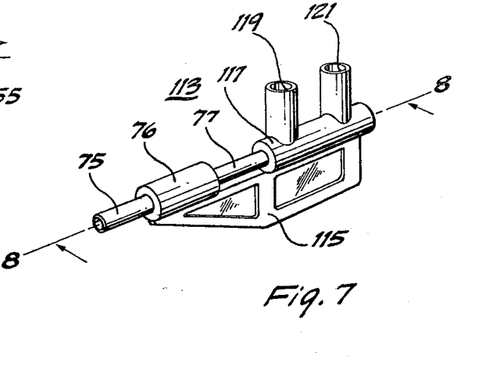
FIG. 7 shows a perspective view of an alternate disposable sensor with a connecting chamber.

FIG. 7 is a perspective view of an alternate embodiment 113 of the fluid or moisture sensor illustrated in FIGS. 3 and 4. A supporting connecting member 115, which may be a ribbed panel, is attached to insulating conduit 76 and to a cylindrical enclosure 117 and holds conduit 76 in a spaced relationship to enclosure 117. Electrically conducting conduit 75 is attached to one end of conduit 76 and electrically conducting conduit 77 connects the other end of conduit 76 with enclosure 117. A pair of cylindrical tubes or connecting ports 119 and 121 communicate with the interior of enclosure 117. The body of Sensor 113 maybe integrally molded from plastic or other moldable low cost material and the like. After being used on a patient, sensor 113 may be discarded.

Figure 8:
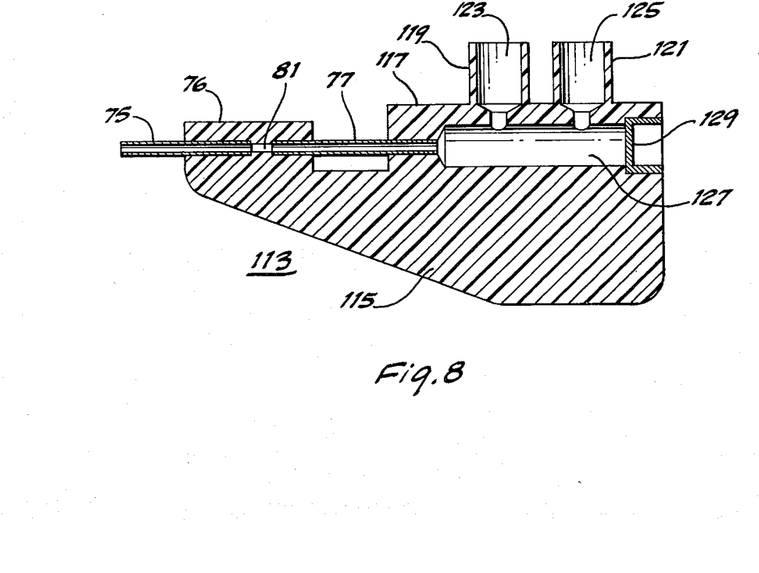
FIG. 8 is a cross-section of the sensor of FIG. 7 taken on the line 8—8 in the direction of the arrows.

FIG. 8 is a cross-section of sensor 113 showing conducting conduits 75 and 77 insulated by connecting conduit 76 and separated by gap 81. Conduit 77 joins connecting conduit 76 to a cylindrical chamber 127 within enclosure 117. Connecting port 119 has an opening 123 which connects with chamber 127 and connecting port 21 has an opening 125 which connects with chamber 127. A sealing plug 129 closes the end of chamber 127 which end is open only for fabrication purposes. Panel member 115 joins conduit 76 with enclosure 117.

Figure 9:
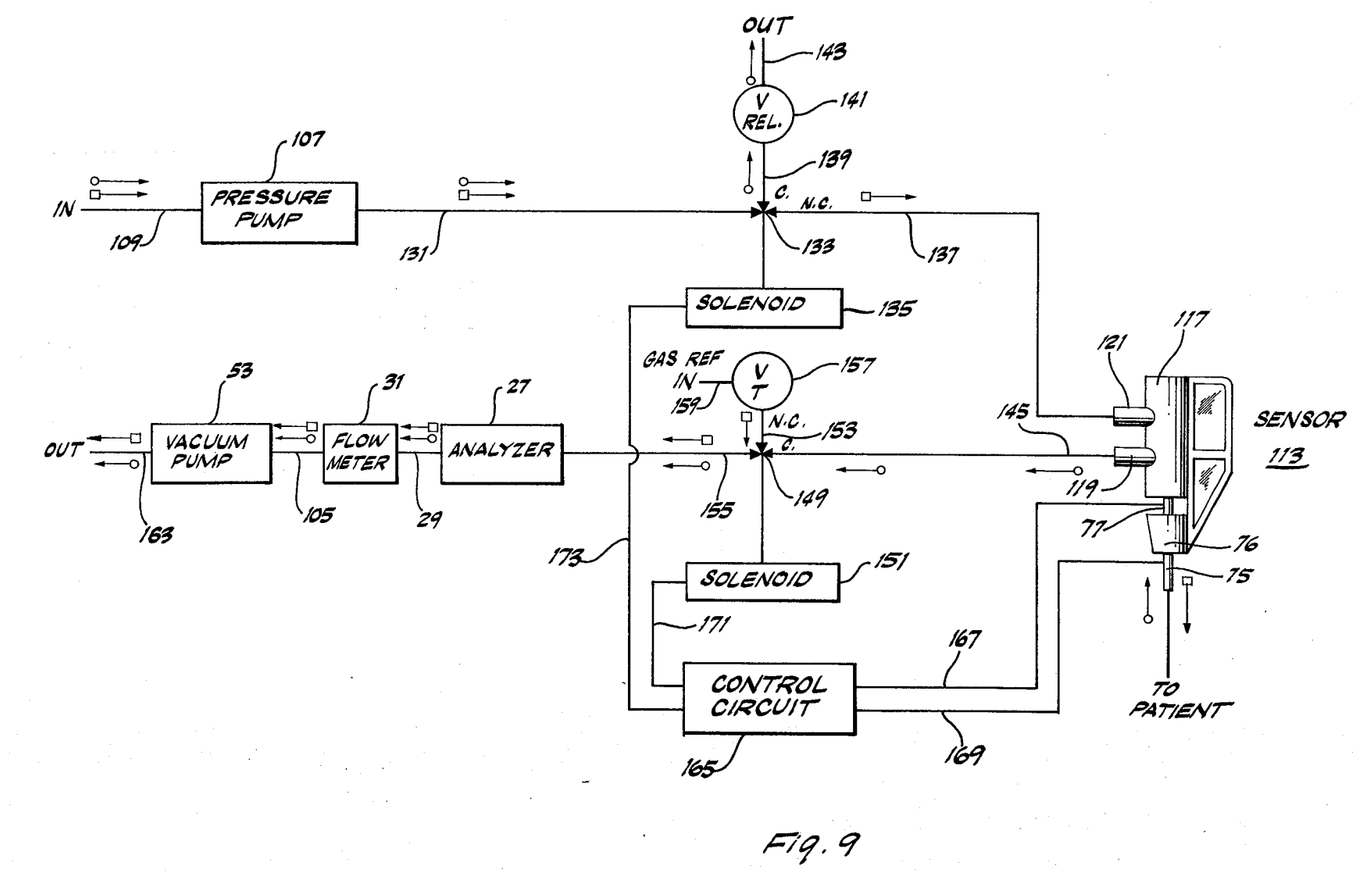
FIG. 9 is a block diagram of the components of a system using the sensor of FIGS. 7 and 8.

FIG. 9 shows input conduit 109 connected to pressure pump 107 which in turn is connected by a conduit 131 to a 3-way solenoid valve 133 which is actuated by a solenoid 135 to connect conduit 131 to a conduit 137. Conduit 131 is normally connected through solenoid valve 133 to a conduit 139 which in turn is connected through a pressure relief valve 141 to an output conduit 143 which vents to outside air.

Conduit 131 is joined through actuated solenoid valve 133 to conduit 137 which in turn is connected to port 121 of sensor 113. Port 119 of sensor 113 is connected through a conduit 145 to a 3-way solenoid valve 149 which is actuated by a solenoid 151. Solenoid valve 149 normally connects conduit 145 to a conduit 155 and when actuated connects conduit 155 to a conduit 153. Conduit 153 is connected through a throttle or adjustable valve 157 to an input conduit 159 which may in turn be connected to a source of reference or calibrating gas or to outside air as desired. Conduit 155 is connected through analyzer 27 to conduit 29 which in turn is connected to flow meter 31 which in turn is connected through conduit 105 to vacuum pump 53. Vacuum pump 53 is connected to an output conduit 163 which may vent to outside air.

Electrical conducting lines 167 and 169 are respectively connected to conductive conduit 77 and 75 and to a control circuit 165. Control circuit 165 is electrically connected to solenoid 151 by electrical line 171 and to solenoid 135 by electrical line 173.

Control circuit 165 may contain the components as shown in FIG. 2 or use other electrical components well known to electrical designer to operate electromagnetic valves from signals generated by electrical sensors.

Operation of the invention may be understood by first referring to FIG. 4 wherein it can be seen that when a droplet of moisture or mucous bridges gap 81, electrically conductive conduit 75 is conductively connected to electrically conductive conduit 77 establishing a low resistance path between electrodes 21 and 23. Typical dimensions of gap 81 are 0.041 inches in diameter and 0.045 inches in length.

Turning to FIG. 2 it can be seen that the low resistance path between electrodes 21 and 23 is in parallel with capacitor 83 and causes a large voltage drop across resistor 85 such that the voltage input to gate 59 falls to a low potential voltage close to ground potential. This in turn causes the output of gate 59 to drop to a low potential voltage which triggers or fires timer 69. The output of timer 69 activates transistor 97 which energizes solenoid 47 of 3-way solenoid valve 45 illustrated in FIG. 1.

The activation of 3-way solenoid valve 45 disconnects pump 53 from conduit 39 and connects pump 53 to conduit 51. This causes moisture and mucous from conduits 11 and 15 to be forced through conduit 17 into sump 57. During this time of purge duration, outside air enters through vent valve 41 and flows through conduits 37 and 33 connected by connector 35, flow meter 31, conduit 29, analyzer 27, conduit 25 and sensor 19, in the directions indicated by the arrows having a "rectangle" tail. Air flows in this manner through conduit 15 and conduit 17 into sump 57 along with gasses entering through conduit 11 into sump 57. This causes the moisture and mucous which activated sensor 19 to be forced into the sump and collected there along with other droplets of moisture and mucous that may have collected in other portions of the conduits and analyzer system components.

Turning to FIG. 2, resistor 71 of timer 69 sets the purge time duration which is typically adjusted to 15 seconds. Timer 69 will remain activated as long as Sensor 19 indicates moisture. However when the condensation or moisture or mucous bridging gap 81 of sensor 19 is removed, the timer will remain activated for the purge time duration to assure other droplets of moisture or foreign material are removed. The purge period is determined by variable resistor 71 and capacitor 93 in a typical well known RC time constant circuit.

Normal operation is illustrated in FIG. 1 by the direction of the arrows having a "circle" tail. Gas to be analyzed enters through conduit 11, connector 13, conduit 15, sensor 19, conduit 25, analyzer 27, conduit 29, flow meter 31, conduit 33, connector 35, conduit 39, 3-way solenoid valve 45, and through conduit 49 and pump 53 to output conduit 55. During this process, analyzer 27 quantitatively and qualitatively analyzes the gas mixture for the constituents that are desired to be detected. However, in monitoring respiratory systems, there is encountered a high level of moisture from the breathing of the patient being monitored along with occasional globules of mucous and other foreign material produced by coughing spasms and conditions of edema of patients. As this unwanted material accumulates in the conduits, it impedes the flow of gas and disrupts the ability of the analyzer to perform its analytical function. Therefore, it is necessary from time to time to purge the system of this foreign material to enable the analyzer to indicate the quantity and quality of constituents of the respiratory gasses.

Although the moisture collected in gap 81 of sensor 19 is indicative of the moisture content of the conduits, it is possible for the gas conduits to collect moisture or mucous which block the flow of gasses without the sensor indicating the presence of this material by producing a low resistance path between electrodes 21 and 23. Therefore, clock 67 and counter 63 provide for an automatic purge by setting switch 61 to any of a number of counter outputs which provide a variety of time periods between automatic purges. For example, by setting switch 61 to output terminal 65a, a low voltage output pulse occurring every four minutes causes the input voltage of gate 59 to drop to activate timer 69 every four minutes automatically whether or not sensor 19 detected the presence of moisture or mucous. Therefore, every four minutes a purge would occur lasting for a purge duration of, say, fifteen seconds. By setting switch 61 to terminal 65b of counter 63, a 15 second purge may be obtained every two minutes. It should be noted that the time durations of the purge periods and the number of selectable purge periods from the counter are the choice of the designer and user.

It should be remembered that gate 59 is designed to produce a low output voltage when either of its inputs are low or if they are both low. Therefore, if either the sensor or the counter or both produce a low input voltage to gate 59, timer 69 is activated to produce a purge of the system.

Operation of the arrangement of FIG. 5 involves two pumps 53 and 107. When no moisture is present the respiratory gasses being analyzed flow in the direction of the arrows with "circle" tails. Pump 53 is a vacuum pump which produces flow in this direction. When moisture is sensed in sensor 19, control circuit 111 removes power from vacuum pump 53 and applies power to pressure pump 107 which in turn pumps air in the direction of the arrows with "rectangle" tails. Air flowing in response to pump 107 forces the moisture out through activating sensor 19 and inlet conduit or catheter 97 in a reverse direction to the normal flow of respiratory gasses produced by pump 53.

It should be noted that in FIG. 5 two pumps are required and the sensor must be disposable as mentioned herein before. However, no sump is required since the unwanted moisture and mucous pumped out of the input conduit or catheter.

In FIG. 6 a sump is used as in FIG. 1 but sensor 19 is in the input conduit or catheter as in FIG. 5. Furthermore, with the deletion of valve 41, there is no reverse flow of air through the analyzer during purge as is the condition of FIG. 1. As set forth in respect to FIG. 5, sensor 19 must be disposable because of its location in the input catheter.

Sensor 113 of FIGS. 7 and 8 operates in the same manner as sensor 19 of FIGS. 3 and 4. Moisture or mucous bridging gap 81 lowers the electrical resistance between conduits 75 and 77. This conductivity change may be detected by a circuit similar to that illustrated in FIG. 2. However, sensor 113 has chamber 127, which is larger in diameter than conduits 75 and 77, and acts as a minature sump which traps any moisture and mucous that may enter to prevent interference with and contamination of the measuring equipment and tubing in the monitoring system. Normally a patient's catheter is connected to conduit 75 and samples of the patient's respiratory gasses are forced through conduits 75 and 77 into chamber 127 and out of opening 123 to a gas monitor or analyzer by connecting a vacuum system or pump to the output of the monitor as illustrated in FIG. 9.

When moisture enters sensor 113 and bridges gap 81, control circuit 165 detects the conductivity change and activates solenoids 151 and 135 to operate solenoid valves 149 and 133. Vacuum pump 53 then forces air or reference gasses through throttle valve 157, conduits 153 and 155, analyzer 27 and flow meter 31 in the direction of the arrows with "rectangle" tails. Valve 149 seals conduit 145 and prevents the flow of air or reference gasses therethrough. During the period of solenoid operation, the flow of air or reference gas through the analyzer enables the analyzer to be calibrated or adjusted to a desired reference reading such as "zero". Therefore, although not illustrated, an automatic "zeroing" circuit may be utilized with analyzer 27 in FIG. 9.

While solenoid 135 is operated, solenoid valve connects pressure pump 107 through conduits 131 and 137 to port 121 of sensor 113. Air or a purging gas which may be connected to conduit 109, is then forced in the direction of the arrows with "rectangle" tails through opening 125 into chamber 127 (FIG. 8) to clear the chamber of any fluid or mucous material. This material is then forced through conduits 77, gap 81 and out of conduit 75 and ultimately out of the end of the patient's catheter, thereby clearing the patients catheter and sensor 113 including gap 81 of all moisture and mucous.

Normally pressure pump 107 is connected through valve 133 to relief valve 141. Relief valve 141 requires a few pounds of pressure before it releases to allow air or purging gas to flow therethrough in the direction of the arrows with the "circle" tails. This "head" of pressure provides a sudden surge of air or gas through sensor 113 when solenoid valve 133 is actuated. This surge of air or gas loosens and dislodges any moisture or mucous droplets clinging to the interior of sensor 113 and the patient's catheter to enable these droplets to be discharged from the catheter by the steady and continuing flow of air or gas provided by pump 107 following the initial surge. The "head" of pressure also provides a rapid purging response to the detection of moisture and mucous material to prevent the material from advancing into connecting port 119 in enclosure 117 before the purging flow of air or gas is established through the sensor. It is important that moisture and mucous not enter connecting port 119 and contaminate the analyzer conduits.

It should be noted that vacuum pump 53 may be the vacuum system of a hospital and during normal operation it forces respiratory samples from a patient through sensor 113, flowmeter 31 and analyzer 27 in the direction of the arrows with the "circle" tails.

It now should be apparent that the present invention provides a circuit arrangement with associated mechanical components which may be employed in conjunction with a respiratory analyzer system for purging unwanted moisture and mucous from the system by sensing the presence of such unwanted material to activate a purge as well as periodically purging the system in response to a counter.

Although particular components, etc., have been discussed in connection with a specific embodiment of a purging system constructed in accordance with the teachings of the present invention, others may be utilized. Furthermore, it will be understood that although an exemplary embodiment of the present invention has been disclosed and discussed, other applications and electrical circuit arrangements and mechanical configurations are possible and that the embodiments disclosed may be subjected to various changes, modifications and substitutions without necessarily departing from the spirit of the invention.

What is claimed is:

1. A purging system for removing foreign matter from a fluid conducting conduit, comprising:

a sensor adapted to be connected in a fluid conducting conduit for sensing foreign matter therein, said sensor having an output terminal at which an electrical output signal is generated when foreign matter is present;

timer means having an input terminal connected to said sensor output terminal, said timer means having an output terminal at which an output signal is generated for an adjustable duration of time when said input terminal receives an electrical signal, said timer means having means for adjusting said duration of time; and pump means electrically connected to said timer means output terminal and being adapted to be connected to the same conduit in which said sensor is connected, said pump means being activated by said timer means output signal for said adjustable duration of time to purge the conduit to remove foreign matter therefrom.

2. The purging system described in claim 1 wherein said pump means comprises:

a sump container having an inlet tube adapted to be connected to the same conduit to which said sensor means is connected, said pump having an outlet tube;

electrically operated valve means connected to said timer means output signal and connected to said output tube of said sump container for connecting said output tube of said sump container to a pump when said valve means is operated; and a pump connected to said electrically operated valve means to pump foreign matter from the conduit into said sump container when said electrically operated valve connects said valve to said sump container.

3. The purging system described in claim 1 wherein said sensor comprises:

a pair of electrically conductive fluid conduits;
an electrically insulative coupling for insulatively joining said pair of electrically conductive fluid conduits together mechanically in series such that adjacent ends are separated by a gap; and
a pair of electrodes connected to said pair of electrically conductive fluid conduits such that one of said pair of electrodes is electrically connected to one of said pair of electrically conductive fluid conduits and the other of said pair of electrodes is electrically connected to the other said pair of electrically conductive fluid conduits.

4. The purging system described in claim 1 wherein said timer means comprises:
counter means having an output terminal at which a periodic electrical signal is generated, said counter means having means for adjusting the period of said periodic electrical signal; and
gate means connected between said sensor output terminal and said timer means input terminal, said gate means having two input terminals and an output terminal, one of said two input terminals being connected to said sensor output terminal and the other of said two input terminals being connected to said counter means output terminal, the output terminals of said gate means being connected to said input terminal of said timer means, said gate means producing an output signal at said gate means output terminal when either or both of said counter means output signal and said sensor output signal are present at the input terminals to said gate means.

5. A purging system for removing foreign matter from a fluid conducting conduit described in claim 1 wherein said sensor includes a moisture sensor having inlet and outlet gas lines and an electrical output at which an electrical signal is generated when moisture is detected therein and wherein said timer means includes a control circuit having an electrical input connected to said sensor electrical output and having two alternately activated electrical outputs, one of said electrical outputs being activated when moisture is detected by said sensor and the other of said electrical outputs being activated when no moisture is detected by said sensor and wherein said pump means includes a pressure pump having an inlet gas line and an outlet gas line and being electrically connected to said one of said electrical outputs of said control circuit whereby said pressure pump is actuated to force gas from said inlet gas line to said outlet gas line when said one of said electrical outputs of said control circuit is activated, further including:
a vacuum pump having an inlet gas line and an outlet gas line and being electrically connected to said other of said electrical outputs of said control circuit whereby said vacuum pump is actuated to force gas from said inlet gas line to said outlet gas line when said other of said one of said electrical outputs of said control circuit is activated;
a gas analyzer having an inlet gas line and an outlet gas line, said outlet gas line being connected to said inlet gas line of said vacuum pump whereby gas is forced through said analyzer when said vacuum pump is actuated; and
a conduit connector for connecting said outlet gas line of said sensor to said outlet gas line of said pressure pump and to said inlet gas line of said gas analyzer whereby gas is normally forced from said inlet gas line to said outlet gas line of said sensor and through said gas analyzer when no moisture is detected by said sensor and gas is forced through said sensor in the reverse direction when moisture is detected by said sensor, thereby clearing the moisture out through the sensor inlet gas line.

6. A purging system for removing foreign matter from a fluid conducting conduit described in claim 1 wherein said sensor includes a moisture sensor having inlet and outlet gas lines and an electrical output at which an electrical signal is generated when moisture is detected therein and wherein said timer means includes a control circuit having an electrical input connected to said sensor electrical output and having an electrical output which is activated when moisture is detected by said sensor and wherein said pump means includes a vacuum pump having an inlet gas line adapted to be connected to a solenoid valve outlet gas line and having an outlet gas line vented to the atmosphere, further including:
a solenoid valve having first and second inlet gas lines and an outlet gas line normally connected to said first inlet gas line, said solenoid valve having a solenoid which is electrically connected to said control circuit electrical output and which is electrically actuated to connect said second inlet gas line to said outlet gas line when said control circuit electrical output is activated, said solenoid valve outlet gas line being connected to said vacuum pump inlet gas line;
a sump container having an inlet gas line and an outlet gas line, said outlet gas line being connected to said second inlet gas line of said solenoid valve;
a gas analyzer having an inlet gas line and and outlet gas line, said outlet gas line being connected to said first inlet gas line of said solenoid valve; and
a conduit connector for connecting said output gas line of said sensor to said inlet gas line of said sump container and to said inlet gas line of said analyzer whereby when no mositure is detected by said sensor, gas flows in said sensor inlet line and through said sensor and through said analyzer and said vacuum pump and when moisture is detected by said sensor, gas flows in said sensor inlet gas line and through said sensor into said sump container where the moisture is collected and out of said sump container and through said vacuum pump.

7. The purging system described in claim 1 wherein said sensor includes a moisture sensing means having an input conduit and an output conduit, said output conduit being adapted to be connected to the input gas line of an analyzer means, said moisture sensing means having an output electrode at which a signal is generated when moisture is present in said moisture sensing means and wherein said pump means includes a pump adapted to be connected to the gas outlet line of a 3-way solenoid valve and wherein said timer means includes control circuit means adapted to be connected between said sensor output electrode and a solenoid for actuating the solenoid when said sensor indicates the presence of moisture, further including:
analyzer means having an input gas line and an output gas line, said input gas line of said analyzer means being connected to said output conduit of said moisture sensing means;
a first connector for coupling three gas conduits together, said first connector having one gas line adapted to be connected to a source of input gas to be analyzed by said analyzer means, said first connector having a second gas line adapted to be connected to a sump container and a third gas line connected to said moisture sensing means input conduit;

a second connector for coupling three gas conduits together, said second connector having one gas line connected to said output gas line of said analyzer means, said second connector having a second gas line adapted to be connected to a vent valve, and a third gas line adapted to be connected to a first gas inlet line of a 3-way solenoid valve;

a vent valve having an inlet gas line vented to outside surrounding air and an outlet line connected to said second gas line of said connector, said vent valve being adjustable to control the flow of gas through said analyzer means by venting outside air into the gas analyzer system;

a sump container having a gas inlet line connected to said second gas line of said first connector and a gas outlet line adapted to be connected to a second gas inlet line of a 3-way solenoid valve; and a 3-way solenoid valve having a gas outlet line normally connected to a first gas inlet line and normally closed to a second gas inlet line, said 3-way solenoid valve having an actuating solenoid for connecting said second inlet line to said gas outlet line and disconnecting said first inlet line from said gas outlet line when said solenoid is actuated, said first gas inlet line being connected to said third gas line of said second connector and said second gas inlet line being connected to said gas outlet line of said sump container, said actuating solenoid being connected to said sensor output electrode.

8. The gas analyzer system described in claim 7 wherein said control circuit means comprises a timer having an input trigger terminal connected to said sensor output electrode, said timer having an output terminal at which an output signal is generated for an adjustable duration of time, said timer having means for adjusting said duration of time, said output terminal of said timer being connected to said solenoid of said 3-way solenoid valve.

9. The gas analzyer system described in claim 7 wherein said moisture sensing means comprises:
a pair of electrically conductive gas conduits;
an electrically insulative coupling for insulatively joining said pair of electrically conductive gas conduits together in series; and
a pair of electrodes connected to said pair of electrically conductive conduits such that one of said pair of electrodes is electrically connected to one of said pair of electrically conductive conduits and the other of said pair of electrodes is electrically connected to the other of said pair of electrically conductive conduits.

10. The gas analzyer system described in claim 7 wherein said control circuit comprises:
a counter having an output terminal at which a periodic electrical signal is generated, said counter means having a switch for adjusting the period of said periodic electrical signal;
a gate having two input terminals and an output terminal, one of said two input terminals being connected to said moisture sensing means output electrode and the other of said two input terminals being connected to said counter means output terminal, said gate producing an output signal at said gate output terminal when either or both of said counter means output signal and said moisture sensing means output signal are present at the input terminals to said gate; and
a timer having an input trigger terminal connected for an adjustable duration of time, said timer having means for adjusting said duration of time, said output terminal of said timer being connected to said solenoid of said 3-way solenoid valve.

11. A respiratory monitoring system comprising:
a moisture sensor for detecting the presence of moisture in gas conduits, said sensor having an input gas conduit adapted to receive respiratory gasses from a patient and a respiratory gas output connector and a purging gas input connector, said sensor having a pair of electrical connectors between which an electrical signal is generated when moisture is detected in said sensor;
a control circuit connected to said pair of electrical connectors, said control circuit having two electrical outputs adapted to be connected to a first and a second solenoid valve, respectively, said two electrical outputs generating an electrical signal when said sensor detects moisture;
a first and a second solenoid valve each connected to one of said two electrical outputs of said control circuit and each valve being actuated when said control circuit outputs generate an electrical signal, each valve having a common gas conduit and first and second gas conduits, said common gas conduit being connected to said second gas conduit for each valve when each valve is actuated and said common gas conduit being connected to said first gas conduit for each valve when each valve is not actuated, said second solenoid valve having said common gas conduit adapted to be connected to a source of gas pressure and said second gas conduit connected to said purging gas input connector of said sensor, said first solenoid valve having said first gas conduit connected to said respiratory gas output connector of said sensor;
a gas analzyer having an input gas conduit and an output gas conduit, said output gas conduit being adapted to be connected to a source of vacuum and said input gas conduit being connected to said first solenoid valve common gas conduit and through said first solenoid valve to said respiratory gas output connector of said sensor when said first solenoid valve is not actuated and disconnected from said respiratory gas output connector of said sensor when said first solenoid valve is actuated;
reference gas means connected to said second gas conduit of said first solenoid valve and through said first solenoid valve to said gas analzyer input gas conduit for calibrating said gas analzyer when said first solenoid is actuated and being disconnected from said gas analzyer input gas conduit when said first solenoid valve is not actuated; and
a pressure relief valve connected to said first gas conduit of said second solenoid valve and through said second solenoid valve to said common gas conduit of said second solenoid valve when said second solenoid valve is not actuated for establishing a head of gas pressure at said common gas conduit of said second solenoid valve, said head of pressure being released through said second solenoid valve from said common gas conduit to said second gas conduit and to said purging gas input connector of said sensor when said second solenoid valve is actuated thereby purging said sensor and said sensor input gas conduit of moisture.

* * * * *